United States Patent [19]

Malvar

[11] Patent Number: 5,325,722
[45] Date of Patent: Jul. 5, 1994

[54] SPLIT PIPE TESTING DEVICE FOR THE MEASUREMENT OF BOND OF REINFORCEMENT UNDER CONTROLLED CONFINEMENT

[75] Inventor: Javier Malvar, Ventura, Calif.

[73] Assignee: The United States of America as represented by the Secretary of the Navy, Washington, D.C.

[21] Appl. No.: 931,464

[22] Filed: Aug. 14, 1992

[51] Int. Cl.$^5$ .......................... G01N 3/10; G01N 3/24
[52] U.S. Cl. ........................................ 73/789; 73/794; 73/841
[58] Field of Search ................. 73/789, 794, 795, 796, 73/799, 827, 834, 841, 845, 846, 842, 803

[56] References Cited

U.S. PATENT DOCUMENTS

| | | | |
|---|---|---|---|
| 3,986,885 | 10/1976 | Lankard | 106/99 |
| 4,081,992 | 4/1978 | Aurora et al. | 73/84 |
| 4,192,194 | 3/1980 | Holt | 73/794 |
| 4,308,751 | 1/1982 | Thurner et al. | 73/627 |
| 4,501,153 | 2/1985 | Mehes et al. | 73/803 |
| 4,553,852 | 11/1985 | Derderian et al. | 374/1 |
| 4,876,896 | 10/1989 | Snow et al. | 73/827 |

OTHER PUBLICATIONS

American Society for Testing and Materials, vol. 04.02; Concrete & Aggregate Annual book to ASTM Standards, pp. 150-154, Standard Test Method for Comparing Concretes on the Basis of the Bond Developed with Reinforced Steel.
James V. Cox & Leonard R. Herrmann, Confinement Stress Dependent Bond Behavior, Part II: A Two Degree of Freedom Plasticity Model; Jun. 1992.
Raymond E. Untrauer & Robert L. Henry, Influence of Normal Pressure on Bond Strength-Feb. 10, 1964, Title No. 62-36 vol. 62, No. 5.
P. J. Robins & I. G. Standish, Bond in Concrete-Jun. 1982, pp. 262-273, Department of Civil Engineering, Paisley College Scotland Effect of Lateral Pressure on Bond of Reinforcing Bars in Concrete.
P. J. Robins & S. A. Austin, Proceedings Second International Conference Madrid, Spain 1986, vol. 2 Bond of Lightweight Aggregate Concrete Incorporating Condensed Silica Fume.
V. Navaratnarajah, P. R. S. Speare, A Theory of Transfer Bond Resistance of Deformed Reinforcing Bars in Concrete Under Lateral Pressure, Magazine of Concrete Research: vol. 39. No. 140: Sep. 1987, pp. 161-168.
National Technical Information Service, Local Bond Stress-Slip Relationships of Deformed Bars Under Generalized Excitations Experimental Results and Analytical Model-Oct. 83, pp. 15-21 & pp. 95, 97 & 112.
Pietro G. Gambarova & Gian Paolo Rosati & Barbara Zasso, Steel-to-Concrete Bond After Concrete Splitting: Test Results-Materials & Structures 1989, vol. 22 pp. 35-47.
Ir. C. R. Braam, Bodn Between Concrete and Reinforcing Steel; State-of-the Art-1989, Report 25.5.89-17/-VFA-2, pp. 97-108.
Karlfried Dorr, Bond-Behaviour of Ribbed Reinforcement Under Transversal Pressure, 1974; pp. 14-24.
University Microfilms International, Local Bond Between a Steel Bar & Concrete Under High Intensity Cyclic Load; pp. 44-50 & pp. 162-163, 169 & 325-329.
L. J. Malvar, Bond of Reinforcement Under Controlled Radial Pressure; Aug. 1992, pp. 1-35.

*Primary Examiner*—Hezron E. Williams
*Assistant Examiner*—Helen C. Kwok
*Attorney, Agent, or Firm*—David Kalmbaugh; Melvin J. Sliwka; John L. Forrest, Jr.

[57] ABSTRACT

A method and apparatus for determining the stress-slip relationship of specimens in concrete including a pipe with a plurality of longitudinal slots evenly spaced around the circumference of the pipe, a specimen and concrete block located in one end of the pipe, a confining device for applying a constant force to the circumference of the concrete block before, during and after a test, a device for measuring the displacement of the specimen relative to the concrete block, and a device for measuring the radial displacement of the concrete block.

16 Claims, 5 Drawing Sheets

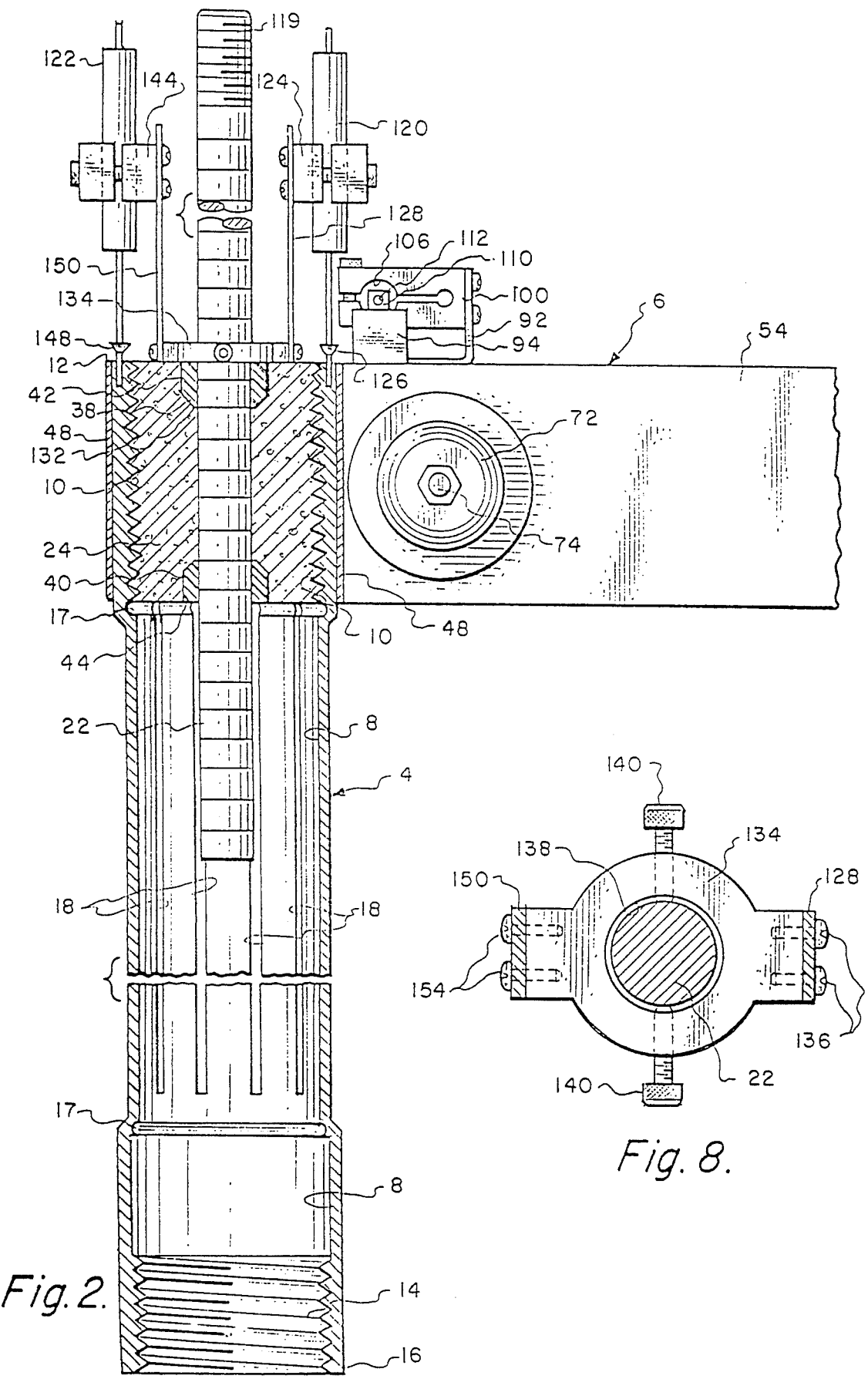

SPLIT PIPE TESTING DEVICE FOR THE MEASUREMENT OF BOND OF REINFORCEMENT UNDER CONTROLLED CONFINEMENT

BACKGROUND OF THE INVENTION

The present invention relates to a method and apparatus for determining the bond stress-slip characteristics of filaments, wires, rods and the like in composite materials such as concrete.

Critical Navy reinforced concrete structures, such as missile test cells and graying drydocks, are designed to withstand large deformations under severe blast and strong-motion earthquake loads.

In these and many other reinforced concrete structures subjected to large deformations in the nonlinear range, one mode of failure is tensile cracking of the concrete and debonding of the reinforcement. The development of design criteria for these structures requires the evaluation of their response in the nonlinear range where severe deterioration of the steel concrete interface takes place. Accurate modeling of the nonlinear response obviously requires an accurate representation of the interface behavior for large deformations.

Where it is important to predict failure or severe damage, proper representation of the bond between the concrete and the reinforcing bar (rebar) is crucial.

The mechanism of bond includes three main components: chemical adhesion, friction, and mechanical interlock between bar ribs and concrete. Initially, for very small values of bond stress of up to 200 psi, chemical adhesion is the main resisting mechanism. If the bond stress is increased, chemical adhesion is destroyed and replaced by the wedging action of the ribs. This wedging action originates crushing in front of the ribs. Once enough crushing has occurred, a wedge of compacted powder forms in front of the rib, with a low angle of incidence (around 30 to 40 degrees), which then produces wedging, inclined transverse cracks, and longitudinal cracks.

If inadequate confinement is provided in testing, bond failure occurs as soon as the cracks spread through the concrete cover of the bar and the test results do not accurately predict a real life scenario. With proper confinement, the bond stress reaches a maximum before decreasing as the concrete between ribs fails and a frictional type of behavior ensues.

Existing bond stress-slip relationships typically ignore the effects of radial stress and deformation. Accordingly, these relationships are strongly dependent on the particular specimen configuration used and vary widely as shown in FIG. 1.

Recent studies have underlined the importance of providing a proper confining pressure to the test specimens.

For example, Untrauer and Henry pulled #6 and #9 grade 60 bars from 6-inch (152-mm) cube specimens subjected to lateral pressure on two opposite faces of up to 2370 psi (16.3 MPa). Bond strength increased with the square root of the pressure.

Robins and Standish pulled 8- and 12-mm (0.31- and 0.47-in) bars from 100-mm (4-in) cubes laterally loaded on two opposite faces. The pull-out load increased more than 100 percent for lateral pressures of about 10 N/mm$_2$ (4060 psi) did not increase the failure loads. Robins and Austin used the same setup on lightweight aggregate concrete specimens. Again, increases over 100 percent in pull-out load were observed for lateral pressures from 0 to 24 N/mm$_2$ (3480 psi), with greater increases taking place at low lateral pressures. Similar observations were reported by Navaratnarajah and Speare.

Eligehausen et. al. tested 125 pull-out specimens consisting of a grade 60 bar with a short length (5d, d=bar diameter) embedded in a 305-mm (12-inch) by 7d by 15d reinforced concrete specimen. An increase in unidirectional confinement from 0 to 13.1 MPa (1900 psi) yielded a 25 percent increase in maximum bond resistance. Confinement provided by the transverse steel across the crack plane was not evaluated.

Gambarova et. al. pulled 18-mm (0.70-in.) bars embedded in a longitudinally cracked concrete specimen. External confinement perpendicular to the cracking plane allowed control of the crack opening, which was kept constant during each test. Bond was observed to increase with increasing confinement, i.e., with decreasing crack opening, by up to 40 percent.

Using a setup similar to Gambarova et. al., Modena et. al. studied the effects of constant confining pressure. A 16-mm diameter bar with lugs at 45 degrees was used. During the tests the slip was increased up to 5 mm (0.2 in.), which is about ½ of the lug spacing. They reported an increase in bond strength from about 3 to 8.5 MPa (0.4 to 1.2 ksi) for a confining pressure varying from 1.8 to 8.6 MPa (0.26 to 1.25 ksi). They also reported an increase in the crack opening up to a limit value which decreases with the confining stress.

Braam reports work by Vos and Schmidt-Thro for specimens under both radial and lateral pressure, respectively. However Vos' work was a numerical study only. Finite element calculations by Vos indicated a linear increase of bond stress with axisymmetric radial pressures varying from 2 MPa (290 psi) in tension to 22.5 MPa (3260 psi) in compression. Schmidt-Thro pulled 16-mm (0.63-in.) diameter deformed bars embedded 48 mm (1.9 in.) in an eccentric concrete specimen with a 251-mm (1-in.) cover. Tests with constant lateral pressure up to 20 MPa (2900 psi) showed gains in bond strength of up to 150 percent with the most pronounced increases occurring at the lower lateral pressures.

In the preceeding studies, confinement was applied uniaxially and not biaxially as in the present invention. The application of only a uniaxial confining pressure requires a more complex model to evaluate the confining pressures at the concrete-rebar interface. As a result, the evaluated pressures are more difficult to determine accurately and the bond stress-slip relationships derived therefrom are accordingly less reliable and useful.

Dorr subjected 16-mm (0.63-in.) deformed bars embedded in a 150-mm (6-inch) diameter cylindrical concrete specimen to tension (i.e. pulled from both ends). The specimens were subjected to confining pressures of up to 15 MN/mm$^2$ (2175 psi). The confining pressures were established by placing the concrete specimen in an oil filled confining ring and pressurizing the oil bath to exert force on the specimen. It was found that bond stresses could be incremented up to 50 percent. Dorr attributed the large scatter in extant bond stress results to the variations in test specimens used. Unfortunately, Dorr could not develop any shear at the concrete-oil interface. In addition, the use of an end plate introduces unknown confinements.

Hungspreug conducted an extensive review of confinement effects on bond. He found that increasing cover and transverse reinforcement, both of which would increase the confinement on the bar, are generally accepted as increasing bond strength. He also points to an increase of bond with concrete tensile strength (or with the square root of the compressive strength). Empirical relationships have been derived showing the increase in bond strength with increasing concrete strength, increase bar cover, and increasing stirrup area. Hungspreug carried out pull-out tests on cylindrical specimens with constant radial confining pressure. He found a linear pressure up a confinement of 400 psi (2.8 MPa) at the bar surface.

Unfortunately, Hungspreug used a rubber hose between the concrete specimen and the confining ring which could not transfer shear stresses when pulled on one end. In addition, an end plate was necessary to retain the specimen when the rebar was pulled which introduced unknown confinement stresses. Finally, for confinements above about 400 psi, increases in maximum bond force appeared to have been inhibited by severe radial cracking.

It can thus be seen that a test method and apparatus is needed for determining the bond stress-slip relationship that accurately represents real life scenarios by accurately including the variable of confining pressure in the testing.

SUMMARY OF THE INVENTION

Accordingly, the present invention provides a method and apparatus that produces stress-slip relationships that may be used to accurately design reinforced concrete structures for given load conditions and includes a pipe having a threaded first end and second end and also having a plurality of longitudinal slots located at spaced intervals around the circumference of the pipe; a test specimen including a rebar and a concrete block located in the first end of the pipe; a confining device located around the first end for applying a constant chosen confining pressure before, during and after a test; means for measuring the displacement of the rebar relative to the concrete block; means for measuring the force to displace the rebar; and means for measuring the radial expansion of the concrete block. In operation, the pipe, with rebar, concrete block, confining device and measuring devices attached, are installed in a test machine wherein the rebar is pulled in tension from one end while initial confining pressure is applied and modulated during the test to maintain the chosen confining pressure. The measured parameters (data) may be plotted to produce a stress-slip relationship for each rebar, concrete block and confining pressure tested. The results may then be used to predict the behavior of rebars in concrete structures under real life conditions.

BRIEF DESCRIPTION OF THE DRAWINGS

Other objects, features and advantages of the present invention will become more fully apparent from the following detailed description of the preferred embodiment, the appended claims and the accompanying drawings in which:

FIG 2 is a cross-sectional view of the pipe and confining device of the present invention.

FIG. 8 is a top view of the clamp of the present invention used to attach the mounting brackets for the LVDT'S to the rebar.

DETAILED DESCRIPTION OF THE PREFERRED EMBODIMENT

Figure 1:
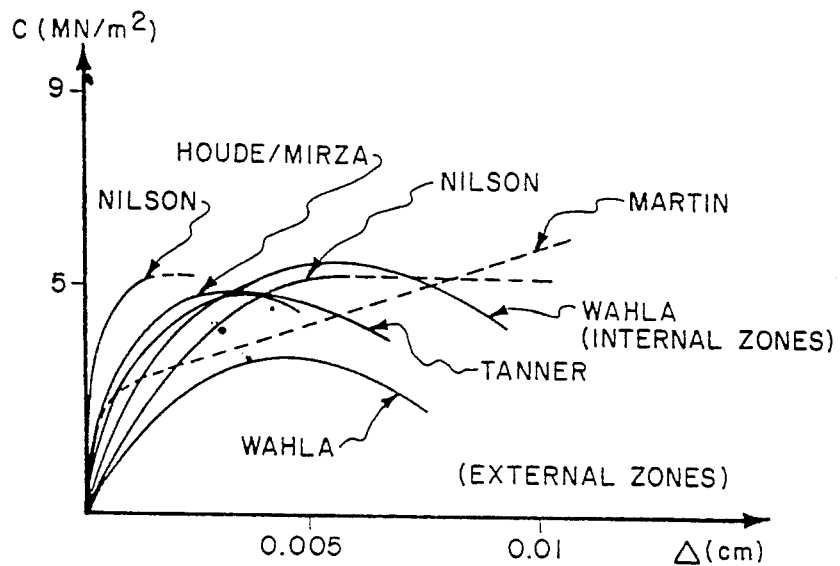
FIG. 1 is a graphical representation of bond stress-slip relationships of various researchers.
Figure 3:
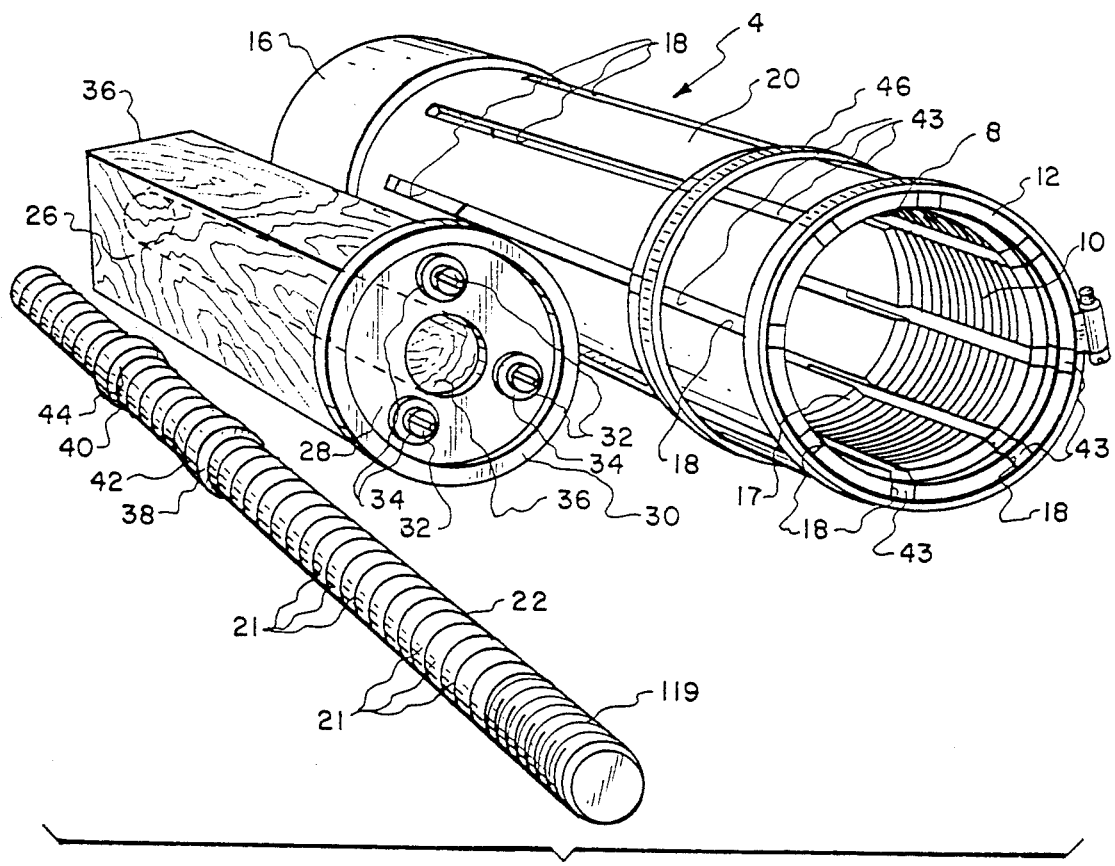
FIG. 3 is an illustration of the present invention including the pipe, wood block, end cap and a rebar with spacers.
Figure 4:
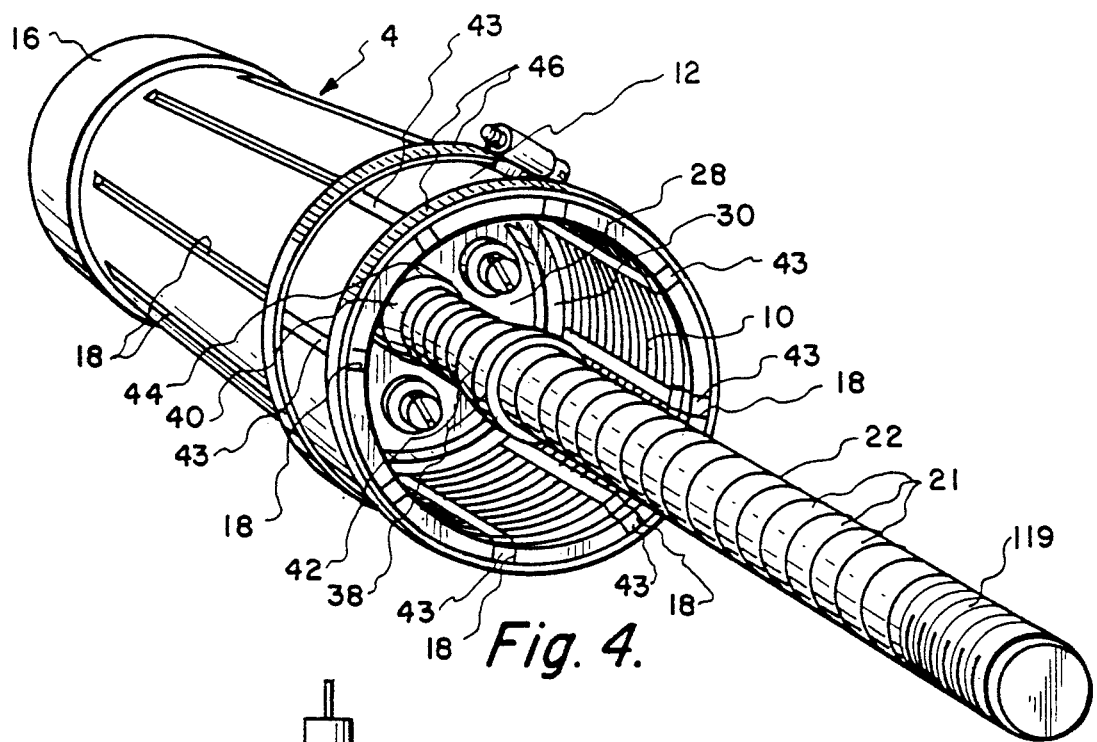
FIG. 4 is an illustration of the present invention including a rebar, end cap and hose clamps installed and ready for concrete to be poured in place.
Figure 5A:
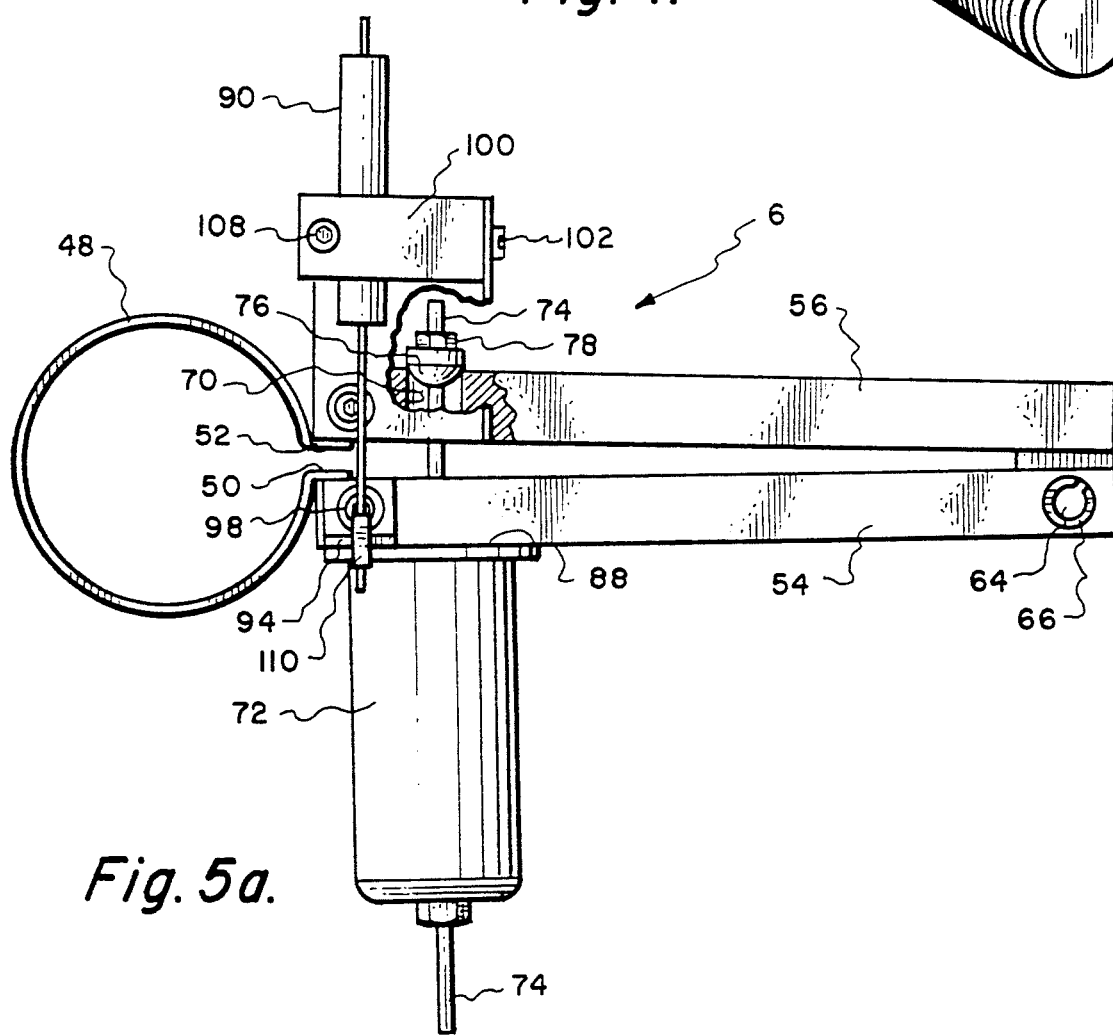
FIG. 5a is a top view of the confining device of the present invention including the hydraulic unit and LVDT for measuring the lateral displacement of arms of the confining device. The "L" brackets are omitted for clarity.
Figure 5B:
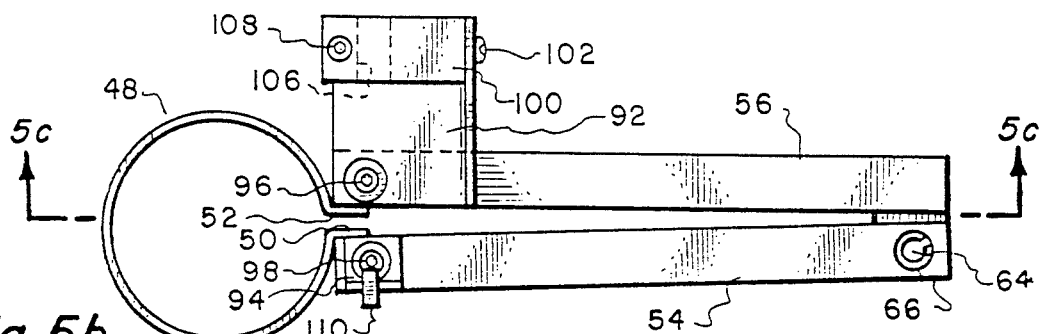
FIG. 5b is a top view of the confining device including the "L" brackets. The hydraulic unit and LVDT are omitted for clarity.
Figure 5C:
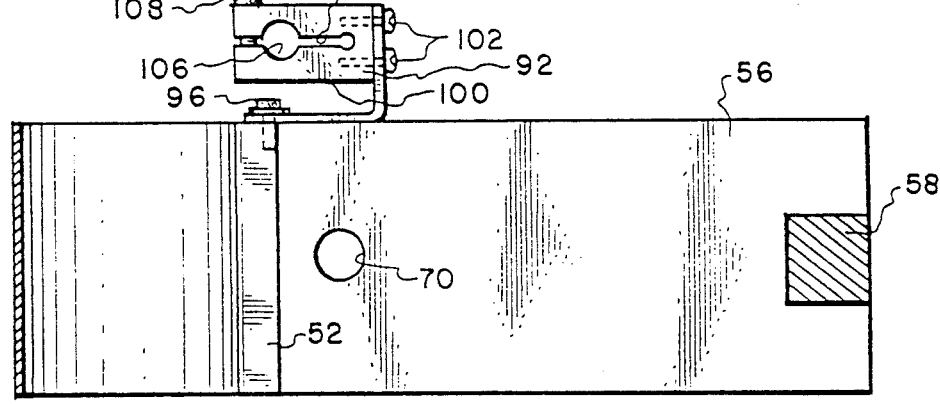
FIG. 5c is a side view of the confining device of the present invention taken through Section 5c—5c of FIG. 5b.
Figure 5D:
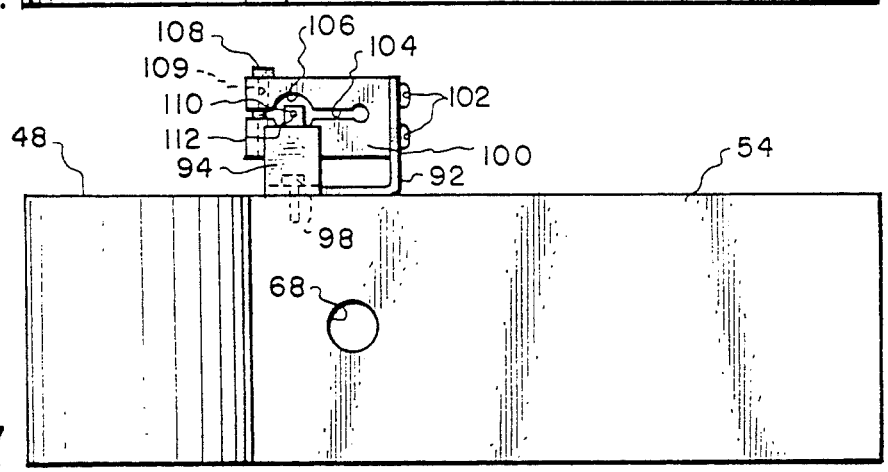
FIG. 5d is a side view of the confining device of the present invention with the hydraulic unit and LVDT omitted for clarity.
Figure 6:
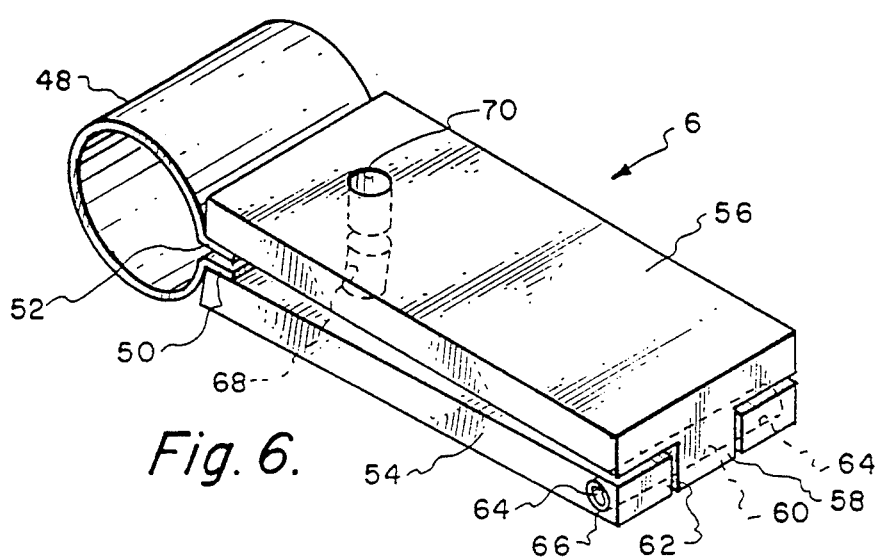
FIG. 6 is a perspective view of the confining device of the present invention including the arms, ring, ear, cutout and pin.
Figure 7:
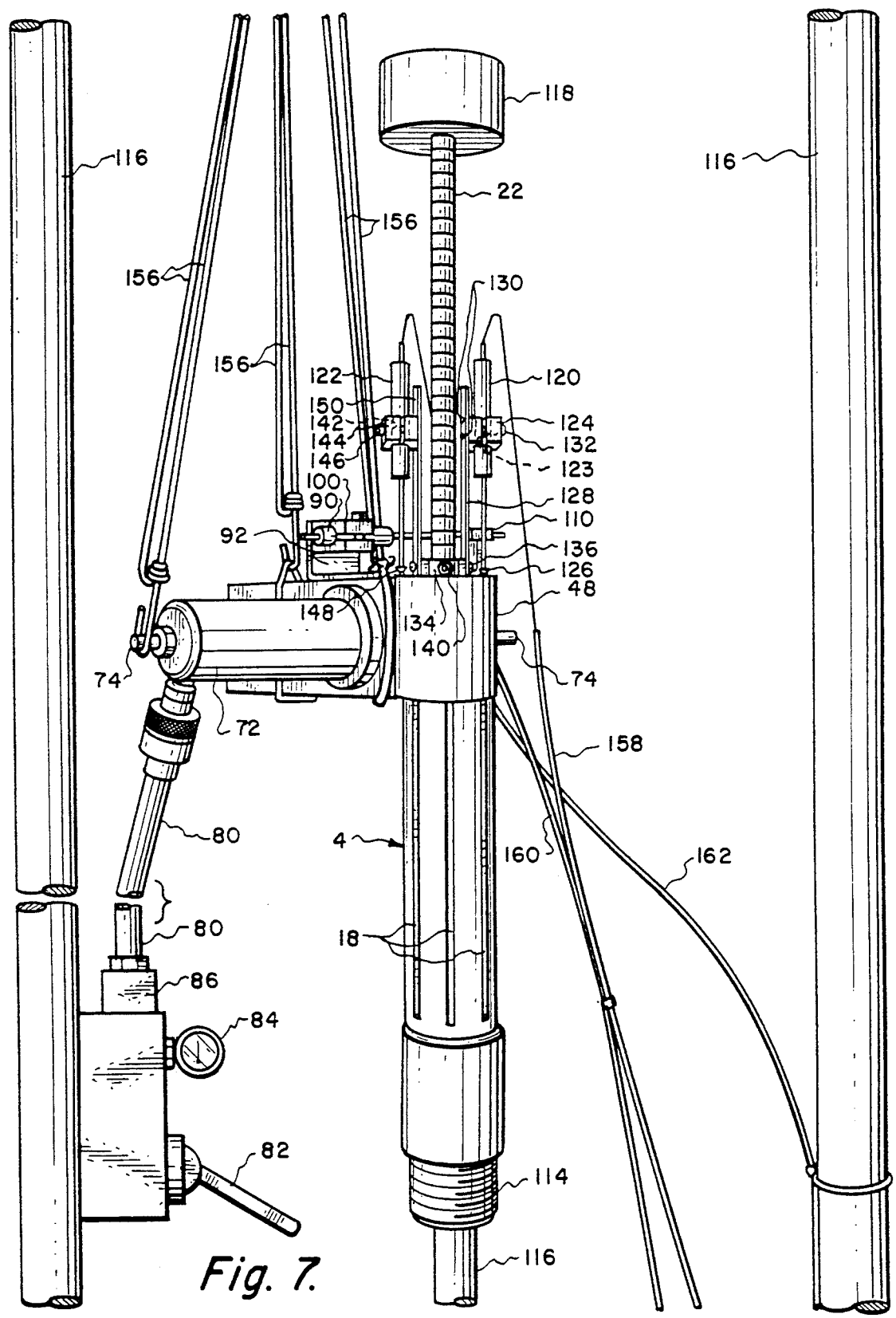
FIG. 7 is an illustration of present invention installed in the testing machine with elastic cords supporting the confining device.

The preferred embodiment of the present invention is illustrated by way of example in FIGS. 2-8. As shown in FIG. 2, the apparatus of the present invention includes pipe 4 and confining device 6. Pipe 4 is cylindrical in cross section and includes inner bore 8 of constant diameter, internal threads 10 at first end 12 and internal threads 14 at second end 16. A plurality of slots 18 are evenly spaced around pipe 4 and extend from first end 12 to adjacent threads 14. Slots 18 reduce confinement from the pipe itself. In the preferred embodiment, confining pressure due to the pipe itself is less than 0.12 psi. Pipe 4 has a outside diameter segment 20 between first end 12 and second end 16. In the preferred embodiment, pipe 4 is extra strong standard steel pipe and is 20 inches long with an outside diameter at first end 12 and second end 16 of 3.5 inches. Reduced diameter segment 20 is 3.2 inches in diameter and approximately 12 inches long. Inner bore 8 is 2 15/16 inches in diameter with 4 UNC (right hand) threads per inch at first end 12 and 6 UNC (right hand) threads per inch at second end 16. A 3/16" radius relief 17 is located at the innermost ends of both threads 10 and 14. Threads 10 are approximately 4 inches long and threads 14 are approximately 2" long. Slots 18 are 3/16" wide and approximately 15 ½ long and extend all the way through pipe 4. There are 8 slots evenly spaced around pipe 4. As shown in FIG. 2, reinforcing bar (rebar) 22 is located in the center of concrete 24 and is shown with confining device 6 attached. Concrete block 24 (i.e. material) and reinforcing bar 22 (i.e. specimen) are installed in pipe 4 by first slidably inserting wood block 26 with cap 28 (see FIG. 3) into pipe 4 until first side 30 of cap 28 is located adjacent the innermost end of thread 10 of first end 12. Note that screws 32 and washers 34 attach cap 28 to block 26. Cap 28 and block 26 are a light, frictional (i.e. interference) fit into pipe 4. Reinforcing bar 22 is a slip fit in bore 36 (see FIG. 3) which extends through the center of cap 28 and block 26. Thus, bore 36 will vary in diameter according to the size of rebar 22 to be tested. Next, silicon rubber spaces 38 and 40 are slidably inserted onto rebar 22 and positioned so that outward extending side 42 of spacer 38 is flush with first end 12 of pipe 4 and outward extending side 44 of spacer 40 abuts first side 30 of end cap 28. It should be noted that spacers 38 and 40 prevent concrete block 24 from contacting rebar 22 in the area covered by spacers 38 and 40. This allows any cracks developed during testing to freely propagate without any influence from free boundary conditions at either end of concrete block 24. In the preferred embodiment, there are 5 full spaces (1 space equals the distance between 2 adjacent ribs 21 of rebar 22) in contact with concrete block 24. Rebar 22 is then inserted into bore 36 of both cap 28 and block 26 until side 44 abuts first side 30 of end cap 28. In this position rebar 22 will be centered in pipe 4 (see FIG. 4). Rubber strips 43 are inserted in each slot 18 to prevent concrete 24 from flowing out of slots 18 when poured. Clamps 46 are attached around first end 12 to limit first end 12 to an outside diameter of approximately 3.5 inches and to hold rubber strips 43 in place. Rebar 22 extends at least 4 inches into block 26. Finally, pipe 4 is orientated vertically, as shown in FIG. 2, and concrete 24 (other materials may be substituted for concrete) is poured into the area between rebar 22 and threads 10 until flush with side 42 of spacer 38. Once concrete 24 is set up and cured (preferrably for 28 days in a fog room), block 26, end cap 28, rubber strips 43 and clamps 46 are removed and ring 48 of confining device 6 is attached around first end 12. Pipe 4 and confining device 6 are then ready to be placed in testing machine 116 as shown in FIG. 7. It should be noted that the terms "concrete" and "concrete block" are used to denote the same material: "concrete" is used to denote material not yet set-up, "concrete block" is used to denote concrete that has setup.

Confining device 6, shown in FIGS. 2, 5a, 5b, 5c, 5d, 6 and 7, includes ring 48 and ears 50 and 52, attached, for example, by welding to arms 54 and 56 respectively. Arm 56 includes ear 58 and bore 60 located therein. Arm 54 includes cutout 62 and bore 64. Arms 54 and 56 pivotally communicate via ear 58 and pin 66 when pin 66 is inserted through aligned bores 60 and 64, as shown in FIG. 6. Arm 54 includes bore 68 and arm 56 includes bore 70. As shown in FIG. 5a, rod 74 of hydraulic unit 72 is inserted through bores 68 and 70 and washer 76 and nut 78 are attached onto rod 74 and tightened finger tight. A suitable and preferred hydraulic unit 72 is model #RCH 123 S/A manufactured and commercially available from Enerpac Group Applied Power; P.O. Box 325, Milwaukee, Wis. 53201. Hydraulic unit 72 includes hose 80, attached on one end to hydraulic unit 72 and on the other end to hand pump 82, pressure gauge 84 and relief valve 86. Thus, hand pump 82 may be operated to vary the pressure in hydraulic unit 72 and relief valve 86 may be set to maintain a constant chosen pressure in the system. When the pressure is increased in the system, rod 74 is caused to be retracted into hydraulic unit 72, thereby decreasing the distance between washer 76 and shoulder 88. As a result, arms 54 and 56 pivot about pin 66 and close ring 48. In operation, relief valve 86 is set to an initial chosen system pressure thus causing ring 48 to exert a constant confining pressure on first end 12 of pipe 4. When rebar 22 is pulled to failure in testing machine 116, concrete block 24 and pipe 4 expand radially outward, increasing the force on ring 48. Relief valve 86 then automatically modulates the pressure to maintain the constant chosen initial pressure. Accordingly, rebar 22 is pulled to failure with a confining pressure that simulates a constant real life load scenario. Many scenarios are possible, for example: low confining pressures simulate conditions where the rebar is located close to the surface of the concrete whereas high confining pressures simulate conditions where the rebar is located deep within the perimeter of a concrete structure or located at the bottom of a heavy structure. Many other load scenarios may be simulated. The confining device of the present invention can produce confining pressures of up to 4500 psi and above and may even exceed the concrete compressive strength if desired. In the preferred embodiment, arms 54 and 56 are fabricated from 6061-T6 aluminum and are approximately 10" long, 4" wide and ½" thick. Bores 68 and 70 are approximately 1" in diameter and pin 66 is a ⅜" pin. Confining ring 48 is 0.062" thick. When arms 54 and 56 are parallel, arms 54 and 56 are spaced apart approximately 0.25".

The lateral displacement of arms 54 and 56 is measured by means of LVDT (linear variable differential transformer) i.e. displacement transducer 90 attached to arms 54 and 56, via "L" brackets 92 and 94, as shown in FIG. 5a–5d. "L" bracket 92 is attached to arm 56 by bolt 96 and "L" bracket 94 is attached to arm 54 by bolt 98. Phenolic block 100, attached to bracket 92 by bolts 102, includes slot 104 and bore 106. Screw 108, located in bore 109, may be tightened to close bore 106 and secure one end of LVDT (not shown in FIG. 5a) to block 100. The other end of LVDT is attached to lug 110 via bore 112. LVDT's are well known in the art and may be employed in other attachment schemes to measure the displacement of arm 54 relative to arm 56.

When performing a pullout test, threads 14 of second end 16 communicate with threads 114 of test machine 116 and threads 119 of rebar 22 communicate with the pulling end 118 of test machine 116. A suitable and preferred test machine 116 is a 50 kip servo controlled hydraulic unit, model #810, manufactured and commercially available from MTS Systems Corporation, Box 24012, Minneapolis, Minn. 55424. Other testing machines may be used. In the preferred embodiment, rebar 22 is pulled from concrete block 24 approximately one space i.e. the distance between 2 adjacent ribs 21 of rebar 22.

The linear displacement of rebar 22 relative to concrete block 24 is measured by means of first and second LVDT'S 120 and 122, respectively. First LVDT 120 is located on a first end in bore 123 of phenolic block 124 and abuts screw 126 on a second end. Screw 126 is screwably attached to pipe 4 as shown in FIG. 7. Phenolic block 124 is screwably attached to bracket 128 by screws 130. Screw 132 may be tightened to lock phenolic block 124 to first LVDT 120 similiar to LVDT 90 and phenolic block 100 previously described. Bracket 128 is attached to clamp 134 by screws 136. Clamp 134, as shown in FIG. 8, includes bore 138 and is secured to rebar 22 by bolts 140. Clamp 134 is placed as close as possible to concrete block 24.

Second LVDT 122 is mounted 180° from first LVDT and includes similar components. One end of LVDT 122 is located in bore 142 of phenolic block 144 and secured in place by screw 146. The other end abuts screw 148 in pipe 4. Phenolic block 144 is attached to bracket 150 by screws (not shown) and bracket 150 is attached to clamp 134 by screws 154 (see FIG. 8). In operation, readouts from first and second LVDT'S, 120 and 122 respectively, are averaged to obtain a value for displacement of rebar 22 relative to concrete block 24.

It should be noted that, in the preferred embodiment, the outputs from LVDT'S 90, 120 and 122 are fed into a data acquisition system (not shown) via wires 158, 160 and 162 respectively. The data acquisition system may be, for example, a computer. A suitable and preferred LVDT is model #250-DC-E manufactured and commercially available from Schaevitz Engineering Co., located at 7905 N. Route 130; Pennsauken, N.J. 08110. Elastic cords 156 are attached to confining device 6 to substantially eliminate any torquing of pipe 4 due to the weight of offset confining device 6 on pipe 4.

Obviously many modifications and variations of the present invention are possible in light of the above teachings. It is therefore to be understood that within the scope of the appended claims, the invention may be practiced otherwise than as specifically described.

What is claimed is:

1. A method for determining the stress-slip relationship of a specimen in a material, the method comprising the steps of:
    a) installing the specimen and the material in a testing apparatus, said specimen located in said material and the testing apparatus attached to the outer surface of said material;
    b) installing said testing apparatus, said specimen and said material in a testing machine, the testing machine attached to both said testing apparatus and to said specimen, said testing machine capable of applying a force to said testing apparatus and said specimen;
    c) applying an initial confining pressure to said material;
    d) applying a force to said specimen and said testing apparatus to cause said specimen to be displaced from said material;
    e) maintaining the confining pressure of step c at the initial confining pressure before, during and after step d;
    f) measuring the displacement of said specimen relative to said material;
    g) measuring the radial displacement of said material;
    h) measuring the force applied in step d.

2. The method defined in claim 1, wherein said confining pressure of step c is applied to the outer surface of said material.

3. The method defined in claim 1, wherein said confining pressure of step c is applied normal to said force of step d.

4. The method defined in claim 2, wherein said confining pressure of step c is applied normal to said force of step d.

5. An apparatus for determining the stress-slip relationship of a specimen in a material when the specimen is dislodged from the material by means of a testing machine comprising:
    a) first means for communicating with the outer surface of said material;
    b) second means for communicating with said testing machine, the second means also communicating with the first means;
    c) third means for applying a constant confining pressure to said material before, during and after a test;
    d) fourth means for measuring the displacement of said specimen relative to said material when said specimen is dislodged from said material by said testing machine;
    e) fifth means for measuring the radial displacement of said material;
    f) sixth means for measuring the force applied to said specimen and to said material by said testing machine to dislodge said specimen from said material;
    g) seventh means for measuring the confining pressure applied to said material in c.

6. The apparatus defined in claim 5, wherein said first means is annular in shape.

7. The apparatus defined in claim 6, wherein said first means includes threads on the innermost portion of said first means for communicating with the outer surface of said material.

8. The apparatus defined in claim 7, wherein said third means includes a plurality of slots located in said first means, the slots evenly spaced around the circumference of said first means.

9. The apparatus defined in claim 5, wherein said third means includes a plurality of slots located in said first means.

10. The apparatus defined in claim 8, further including a pipe having first and second ends, wherein said first means is located in the first end of the pipe and said second means is located in the second end of said pipe.

11. The apparatus defined in claim 10, wherein said second means includes threads on the innermost portion of said pipe for communicating with said testing machine.

12. The apparatus defined in claim 11, wherein said third means includes a ring located around said first means.

13. The apparatus defined in claim 12, wherein said third means includes a ring having an opening, first and second arms and a hydraulic unit, the first and second arms pivotally attached on one end and the first and second arms communicating with the ring on the other end, the hydraulic unit communicating with the first and second arms to apply a constant force to the arms before during and after the test.

14. The apparatus defined in claim 13, wherein the fourth means is a linear variable differential transformer having first and second ends, the first end communicating with said first means and the second end attached to the specimen.

15. The apparatus defined in claim 14, wherein the fourth means includes two linear variable differential transformers located 180° apart.

16. The apparatus defined in claim 15, wherein the fifth means is a linear variable differential transformer having first and second ends, the first end communicating with said first arm and the second end communicating with said second arm.

* * * * *